United States Patent [19]

Chen

[11] Patent Number: 5,803,896
[45] Date of Patent: Sep. 8, 1998

[54] METHOD AND DEVICE FOR THE TREATMENT OF DIABETES MELLITUS

[76] Inventor: Yu Chen, P.O. Box 10982, Baltimore, Md. 21234

[21] Appl. No.: 694,746

[22] Filed: Aug. 9, 1996

[51] Int. Cl.$^6$ ................................................ A61N 2/00
[52] U.S. Cl. ................................................................ 600/9
[58] Field of Search ............................................ 600/9–15

[56] References Cited

FOREIGN PATENT DOCUMENTS

| 0650188 | 6/1994 | Australia | 600/15 |
|---|---|---|---|
| 2242946 | 4/1925 | France | 600/15 |
| 405245218 | 9/1993 | Japan | 600/9 |

OTHER PUBLICATIONS

Dr. Chen Zhi, Magnetic Therapy, (1979 and 1994), p. 218.
Paul L. Munson (ed.), Principles of Pharmacology, New York, Chapman & Hall (1995), pp. 697–724.

*Primary Examiner*—John P. Lacyk
*Attorney, Agent, or Firm*—Breneman & Georges

[57] ABSTRACT

A method and novel hypoallergenic magnetic device for the treatment of diabetes mellitus is provided by the attachment, mounting or implanting to the ear of the subject along with the provision for supplementing the pancreatic hormones of the subject to assist in the maintenance and stabilization of the blood sugar in diabetic patients. The means for mounting or attaching the magnetic device of the invention includes attachment of the magnetic device by adhesives, adhesive plaster and, where the hypoallergenic materials of the magnet permit, implantation. The device of the invention includes novel hypoallergenic magnetic devices preferably of a circular configuration having a magnetic strength of about 100 to 14,000 gauss which is maintained at one or more locations in the ear 24 hours a day to assist in the lowering and stabilization of the blood sugar within a normal range between doses. The device of the invention may include in a kit one or more circular magnetic devices for external use having a strength from about 100 to 9,000 gauss together with a means for mounting the circular magnetic device in the auricle of the ear which may include a diagram and model of the ear illustrating various locations for attachment in the ear to assist in the placement of the circular magnetic device at one or more locations in the auricle of the ear.

21 Claims, 3 Drawing Sheets

METHOD AND DEVICE FOR THE TREATMENT OF DIABETES MELLITUS

BACKGROUND OF THE INVENTION

1. Field Of The Invention

The present invention pertains to a method and magnetic device for the treatment of diabetes which utilizes a magnet at one or more locations in the auricle of the ear together with insulin injection or oral hypoglycemic agent to assist in the control and maintenance of the blood sugar of the subject within a more normal range to reduce diabetes-related illnesses and complications from diabetes. More particularly, the invention pertains to the utilization of small circular magnets having a strength of from about 100 to 14,000 gauss and preferably 300 to 9,000 gauss which are strategically positioned in the auricle of the ear.

A single magnet or multiple magnets may be used in the treatment of diabetes in accordance with the invention. In applications utilizing a single magnet, the magnet is placed in the auricle of the ear at a location corresponding to the pancreas gland point which is found only in the left ear of a human. In applications involving the use of multiple magnets one magnet is placed in the pancreas gland point in the left ear while the other magnets are placed in either or both the thalamus point and central rim point in either the left or right ear.

The invention involves the attachment of one or more magnetic devices in the auricle area of the ear in combination with the supply or supplement of the insulin of the subject by the utilization of insulin in insulin-dependent diabetics or an oral hypoglycemic agent in non-insulin-dependent diabetics to assist in the maintenance of the blood sugar in a more controlled normal range to prevent complications from diabetes. The small preferably circular magnets are worn 24-hours a day in the auricle of the ear, and preferably the left ear at the pancreas gland point. Additional magnets may be used in the Thalamus point and central rim point in either the left ear or right ear or alternated between the left and right ear on a weekly basis where the second magnet is not implanted.

The magnetic device may be attached, implanted or mounted to the exterior of the auricle of the ear by the utilization of hypoallergenic adhesives or adhesive plasters or be implanted where novel hypoallergenic magnets constructed in accordance with the invention are utilized. In either application of the invention the magnetic device is utilized together with providing or supplementing the subject's own insulin, as well as testing the blood sugar of the subject to determine if the blood sugar is in the normal range. Many times the application of one or more magnets results in the reduction of the normal prescribed dosages for the insulin or oral hypoglycemic agent and results in the maintenance of the blood sugar in the desired lower range. These advantages are achieved in combination without risk of drug interaction and assist in halting extreme complications such as gangrene resulting from advanced stages of diabetes while allowing the body to regenerate tissue.

The invention contemplates the utilization of a kit having one or more small circular magnets having a magnetic strength of from about 100 to 9,000 gauss and, where magnetic implants are utilized, hypoallergenic magnets of 100 to 14,000 gauss. The invention may be implemented in kit-form where magnets designed for external use are included with a means for mounting the circular magnet in the auricle of the ear together with an illustration and plastic ear model illustrating the primary pancreas gland point and secondary positions in the ear. The kit of the invention may further optionally include one or more hypoallergenic circular magnets which may be coated with a hypoallergenic substance such as titanium, platinum or 24 karat gold or be composed of a hypoallergenic material such as platinum alloy magnets. Hypoallergenic magnets as well as the other magnets (coated with a hypoallergenic substance) of varying strengths in the range of 100 to 14,000 gauss may be implanted or mounted in the auricle of the ear. Where a kit is made available to the general public the magnets should be of varying strengths of from between 100 to 9,000 gauss and the kit can optionally include a blood sugar monitoring device for allowing the subject to monitor the result of the treatment.

2. Description Of Related Prior Art

Diabetes and more specifically diabetes mellitus is a serious disease which, if untreated, leads to a number of complications and can result in death. In the United States more than ten million Americans have been diagnosed as having diabetes mellitus. It is estimated that at least another five million people in the United States are undiagnosed and remain undiagnosed until serious symptoms develop which require medical evaluation.

Diabetes presents several long-term problems such as high blood pressure (hypertension), atherosclerosis which produces fatty deposits that thicken the lining of arteries resulting in smaller, less flexible pathways for blood, coronary artery disease, vision problems, kidney failure and deterioration of the nerves and blood vessels in the extremities resulting in the failure of small wounds to heal properly. The long-term effects as well as the short-term dangers of diabetes, such as hypoglycemia, ketoacidosis and hyperosmolar coma have been treated by either insulin injection for those sufferers of diabetes having insulin-dependent diabetes mellitus (IDDM) or the utilization of hypoglycemic agents in those individuals having non-insulin-dependent diabetes mellitus (NIDDM).

In both IDDM and NIDDM cases, traditional Western medicine first requires the detection and diagnosis of diabetes followed by insulin injections for IDDM subjects or the use of an oral hypoglycemic agent in the case of NIDDM subjects to supply the insufficient insulin hormone of the subject. As used herein the term subject refers to not only human patients but also animal subjects that may be treated in accordance with the invention. The use of insulin in IDDM subjects as well as the use of oral hypoglycemic agents in NIDDM subjects lowers the blood sugar and can result in hypoglycemia. Neither insulin nor hypoglycemic agents alone control, regulate or maintain blood sugar in the normal range between doses.

In traditional Chinese medicine needling acupuncture points in the ear have been utilized to treat diabetes. In a book by Dr. Huang Li Chu entitled *Diagnosis and Treatment by Using Ear Acupoints*, the treatment of diabetes by lowering blood sugar by using needle acupuncture at the pancreas gland point, pancreas and gall bladder point, liver point, endocrine point, thalamus point, central rim point, triple burner and subcortex points is discussed. The Traditional Chinese Medical School Guan Su (Province in China) used ear needle acupuncture to reduce blood sugar in 25 cases. Comparative results of blood sugar before and after treatment on an empty stomach, and then two hours after eating, demonstrated needle acupuncture lowered blood sugar. These prior art treatments of diabetes in Chinese medicine required the use of needles and needle acupuncture and not magnets.

The only other known relevant prior art are the two books of Dr. Chen Zhi (1979 and 1994) both of were entitled *Magnetic Therapy* and which advocated the drinking of magnetic water and the application of magnetic disks on the back and stomach and other portions of the human anatomy. This book did not discuss the utilization of magnetic disks in the ear or the utilization of insulin or a hypoglycemic agent to treat diabetes.

Advanced cases of diabetes and aging present many challenging problems. Regulation and control of blood sugar in a normal range is a problem due to problems with circulation and infection in subjects with advanced diabetes. These difficulties apparently result from a combination of factors including aging, bad circulation and complications resulting from advanced stages of diabetes and possible problems with drug interaction and drug interference. Under such circumstances stimulation of diabetics with needle acupuncture, especially in advanced stages of the disease, creates significant risks of infection and challenges in the treatment of diabetes. These problems are aggravated by aging and the treatment with insulin and hypoglycemic agents utilized over long periods of time where heart trouble, bad circulation, atherosclerosis and other complications from the disease often result in the development of neurotropic ulcers and wounds that will not heal resulting in gangrene and amputation.

Over a period of years diabetes can lead to vision loss and a deterioration of nerves and blood vessels, particularly in the extremities. The resulting loss of nerve sensation and circulation as well as the deterioration of blood vessels which limit the flow of blood increases risk of infection and neurotropic ulcers. In such cases needle acupuncture risks further infection while Western medicine and antibiotics have not in all cases been effective due to problems with circulation and have resulted in amputation.

As a result the known prior art has not provided a systematic treatment for advanced stages of diabetes, particularly where neurotropic ulcers and gangrene are present and has not provided a treatment for diabetes by providing a more controlled level of blood sugar corresponding to the three hormones of insulin, glucagon and somatostatin naturally produced by healthy individuals. The relationship of insulin glucagon and oral hypoglycemic agents are described in *Sims EAH, Calles—Escandon J. and the Treatment of Diabetes* and in *Munson PL (ed.) Principles of Pharmacology.* New York, Chapman & Hall (1995), pp. 697–724.

Instead of completely relying upon the artificial raising and lowering of blood sugar between doses by the utilization of insulin or hypoglycemic agents, the invention provides a more controlled and normal level of blood sugar for those suffering from diabetes mellitus. The problems in the control of the blood sugar level together with long periods of undiagnosed suffering from the disease and its long-term and short-term consequences to the body particularly in the aged requires a more controlled stimulation and regulation of the blood sugar of the subject. It has been discovered that utilization of one or more magnetic objects disposed in the auricle of the ear in combination with provision of insulin for IDDM subjects or an oral hypoglycemic agent for NIDDM subjects provides a more regulated method for maintaining blood sugar for longer periods of time and at a lower level in the normal range and without the complications of drug interaction as will be described hereinafter in greater detail in the Summary of the Invention.

SUMMARY OF THE INVENTION

The invention pertains to a method for the treatment of diabetes utilizing one or more magnets in combination with the administration of insulin or a hypoglycemic agent. One or more magnets, preferably of a circular configuration, are attached, mounted or implanted in the auricle of the ear to assist in the regulation of the blood sugar of the diabetic subject. As used herein the term 'subject' refers to not only human patients but also animal patients which may be treated in accordance with the invention. In the case of human patients the magnetic device is implanted or attached over the pancreas gland point which is only in the left ear. In the case of animals the magnetic device may be implanted or attached to the pancreas gland point which in the case of the dog, cat and horse is located in the right ear. In the preferred application of the invention the magnets are of a hypoallergenic construction by employing a platinum or 24 K gold or other hypoallergenic coating or plating or constructed of a platinum alloy to reduce the possibility of skin reaction in advanced diabetic cases. The magnets for external attachment preferably have a diameter of about 0.5 cm or less and have a magnetic strength of from about 100 to 9,000 gauss. Hypoallergenic implantable magnets may be the same size or considerably smaller and have a magnetic strength of from about 100 to 14,000 gauss.

The method of the invention is applicable to the treatment of both insulin-dependent diabetes mellitus (IDDM) subjects and non-insulin-dependent diabetes mellitus (NIDDM) subjects by assisting them in the regulation of blood sugar. The insulin taken in the case of subjects having insulin-dependent diabetes mellitus include any number of insulins obtained from various human and animal sources as well as mixtures thereof. These injectable insulins include insulins produced by recombinant DNA techniques which produce synthetic insulins as well as the semi-synthetic recombinant DNA insulin techniques that are obtained by replacing an amino acid of an animal-based insulin. Such injectable insulins are generally utilized for providing insulin for the IDDM subject and are included within the definition of supplementing the pancreatic hormones of the subject in accordance with the invention.

The method of the invention is also applicable to providing the more effective regulation of the blood sugar in subjects that have non-insulin-dependent diabetes mellitus who would generally take an oral hypoglycemic agent to stimulate insulin secretion or where otherwise insufficient pancreatic hormones are available to the subject. These oral hypoglycemic agents are generally sold under a number of prescription names and include for example Glyburide, Chlorpropamide, Acetohexamide, Glipizide, Tolbutamide, Tolazamide, etc. These oral hypoglycemic agents as well as Humalog, which is being tested by the FDA, and various types of injectable insulins are generically referred to in the method as substances for supplementing the pancreatic hormones of the subject. The method of the invention includes in addition to using insulin or oral hypoglycemic agent as heretofore discussed the application of one or more magnets maintained in the auricle of the ear which assist in the regulation of the blood sugar of a subject having either insulin-dependent diabetes mellitus or non-insulin-dependent diabetes mellitus.

The invention in the best mode contemplates the placement of one or more magnets at specific locations in the auricle of the left ear to assist in the regulation of the blood sugar much more effectively than merely the taking of an injectable insulin or an oral hypoglycemic agent. The invention involves the utilization of one or more small magnets preferably of a circular configuration having a magnetic strength of from about 100 to 9,000 gauss externally attached in the pancreas gland point in the auricle of the left ear. Alternatively hypoallergenic magnets may be implanted in the pancreas gland point in the auricle of the left ear. The specific locations for attachment to the left ear include the pancreas gland point, thalamus point and central rim point in the auricle of the left ear. In addition the thalamus point and central rim point in the auricle of the right ear can be used along with the pancreas gland point in the left ear.

In cases of advanced diabetes or hypersensitivity of a subject to generally available magnetic materials which are generally composed of ferrous alloys, the magnet can be covered with a hypoallergenic substance which preferably is a platinum or 24 K gold coating to reduce sensitivity of the skin to the magnet. These hypoallergenic coatings or the use of magnets composed of hypoallergenic materials such as platinum alloys are useful in treating subjects with advanced diabetes to prevent infection or skin damage due to advanced stages of the disease or poor circulation. In the preferred application of the invention platinum-plated or platinum alloy magnets having a magnetic strength of about 100 to 9,000 gauss are utilized. Platinum alloy magnets and particularly platinum cobalt magnets have magnetic strengths in the range of 9,000 gauss while other magnets composed of aluminum, nickel, cobalt and niobium alloys have magnetic strengths of up to 14,000 gauss. The method of the invention further contemplates the monitoring of the blood sugar of the subject to reduce the dosage of insulin or oral hypoglycemic agent after magnetic regulation of the level of blood sugar demonstrates the justification for lowering the dosage of insulin or hypoglycemic agent.

The invention may be implemented by providing a kit for the stabilization of blood sugar in diabetic patients which preferably includes a plurality of circular magnets for external attachment having varying strengths from 100 to 9,000 gauss and a means for mounting the circular magnet in the auricle of the ear. The kit further can include a diagram which preferably is a plastic ear model illustrating the most effective locations in the auricle of the ear for mounting the circular magnet as well as a blood sugar monitoring device to assist the subject in monitoring the level of blood sugar in order to determine the strength of the magnet which works best. The kit further can include instructions for selecting the proper strength of the magnet as well as the utilization of more than one magnet in more than one location in the left and right ear for increasing the effectiveness of the regulation of the blood sugar.

In the preferred embodiment of the invention such small circular magnets in the range of 100 to 9,000 gauss are placed in the left ear and covered with a circular adhesive plaster and left in the ear 24 hours a day. The adhesive plaster and magnet being removed once a week or once or twice a month in order to clean the ear. Once the magnet is cleaned it should be replaced on the same spot in the ear. Alternatively, where a strong small magnet made of a hypoallergenic material is utilized, the magnet can be implanted in the auricle of the left ear at the pancreas gland point.

In the application of the invention the IDDM subject continues to take insulin while a magnet of 100 to 14,000 gauss is placed in the left ear to stabilize blood sugar in the IDDM subject much more effectively than in subjects without a magnetic disk. Similarly in NIDDM subjects a magnet of 100 to 14,000 gauss is placed in the auricle of the left ear to regulate blood sugar while the NIDDM subject continues to take the oral hypoglycemic agent. In both IDDM and NIDDM types of subjects, the application of the magnetic disk in the left auricle of the human ear operates to regulate blood sugar much more effectively than can be achieved by merely taking insulin or an oral hypoglycemic agent. The method of the present invention assists in the regulation of blood sugar and more effectively controls the disease by reducing the long-term and short-term complications due to diabetes. These advantages of the invention will be illustrated in Examples and the Detailed Description of the Invention as well as the drawings described in the following Description of the Drawings.

DESCRIPTION OF THE DRAWINGS

The advantages of the invention will become apparent to those skilled in the art from the following detailed description of the invention in conjunction with the accompanying drawings in which.

DETAILED DESCRIPTION OF THE PREFERRED EMBODIMENTS

Figure 1:
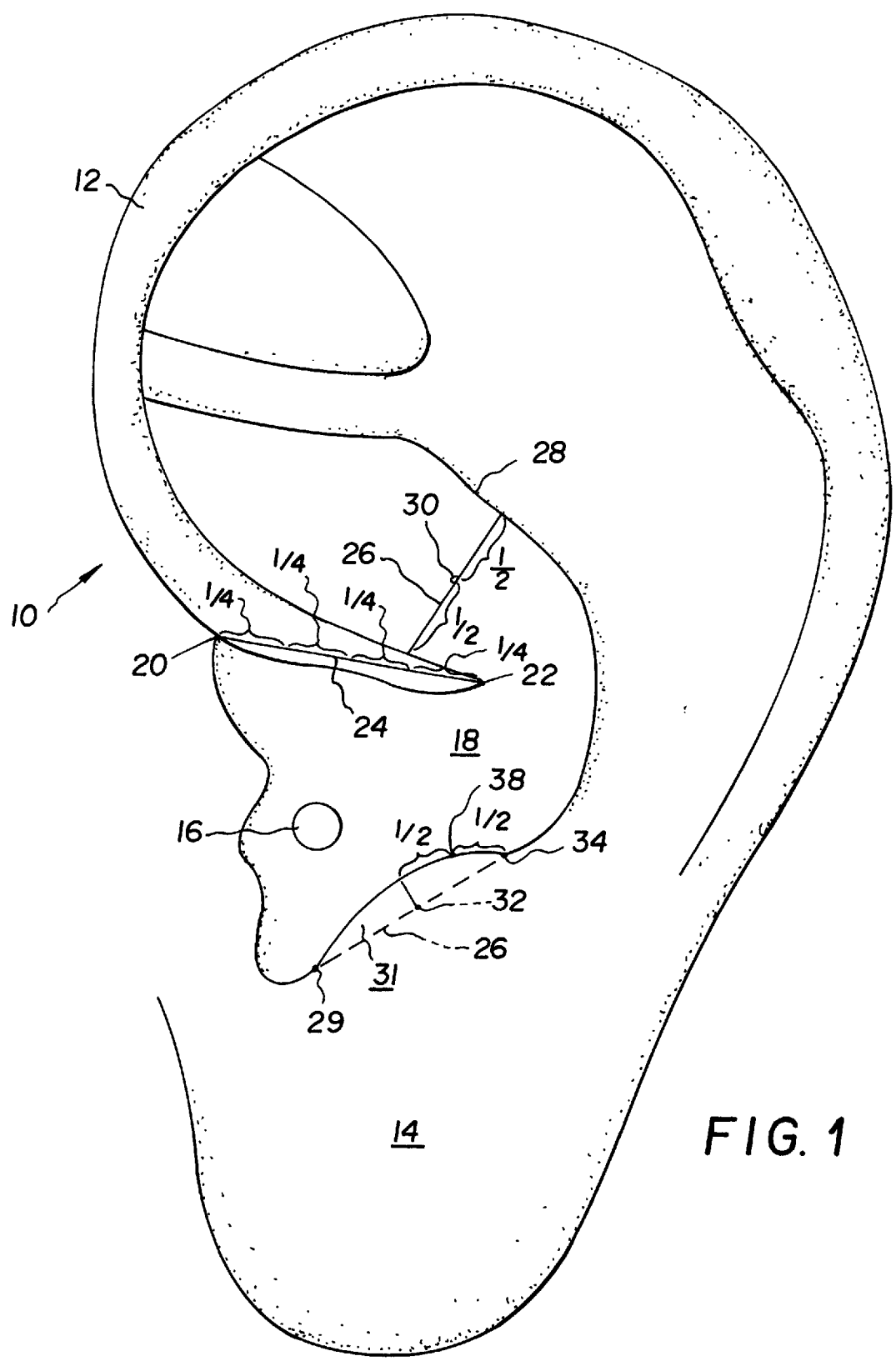
FIG. 1 is a side view of the left ear of a human subject.

The invention pertains to a method and apparatus for assisting in the more controlled regulation of blood sugar between doses for patients suffering from diabetes mellitus which includes the utilization of magnets attached to the ear in combination with insulin or an oral hypoglycemic agent. The regulation provided by the magnets utilized in accordance with the invention allows a more controlled utilization of the dosages for injectable insulins or oral hypoglycemic agents for the diabetic subject to be more controlled and, as a result, reduce the long-term and short-term symptoms and effects of diabetes mellitus and in many cases reduce the dosage of insulin or oral hypoglycemic agent requirements of the patient.

Some of the short-term emergency symptoms of diabetes mellitus include ketoacidosis which generally results when insulin-dependent diabetics miss an insulin shot or when they have an infection which symptom can result in a gradual loss of consciousness. In addition, hypoglycemia or "insulin reaction" can also lead to convulsions and unconsciousness as well as hyperosmolar coma in older persons who can experience a gradual loss of consciousness. These short-term symptoms are generally complications from diabetes resulting from stroke or other illnesses induced by diabetes in older persons. These short-term symptoms require medical attention and stem from an improper blood sugar balance resulting from problems with the pancreas in producing insulin or the failure to take insulin or an oral hypoglycemic agent as prescribed.

The short term problems of ketoacidosis, hypoglycemic coma or hyperosmolar coma are generally complicated by age and years of long-term effects of diabetes mellitus. These long-term effects of diabetes include hypertension, atherosclerosis, kidney disease, vision problems, heart and coronary artery disease. The long-term effects of high blood pressure (atherosclerosis) or the fatty deposits on arteries in conjunction with coronary artery disease can result in claudication, or an unusual discoloration of the foot, skin ulcers and wounds that do not heal and diseases of the extremities. These long-term effects result from an imbalance or improper regulation of blood sugar over long periods of time. Many of the long-term complications result in diabetic neuropathy, or a deterioration of nerve fiber function, as well as neurotropic ulcer formation and secondary gangrene on sores.

Age as well as advanced stages of diabetes and poor circulation result in minor wounds not healing properly. These problems of age and in subjects who have suffered from diabetes over long periods of time can result in neurotropic ulcer formation and gangrene in subjects suffering from both insulin-dependent diabetes mellitus and non-insulin-dependent diabetes mellitus. Treatment of such diabetic subjects presents a serious and challenging problem since insulin alone or hypoglycemic agents alone are insufficient to treat and in many cases to prevent ulcers, gangrene and complications resulting in subsequent amputation.

The invention accomplishes a more controlled or natural regulation of blood sugar by the utilization of one or more magnets strategically disposed in the auricle of the human ear and preferably in the pancreas gland point in the auricle of the left ear. In more severe cases of diabetes, a hypoallergenic magnet, a magnet coated with a hypoallergenic material such as platinum or 24 K gold may be utilized in the case of aged people with circulatory complications or where the disease has gone undiagnosed for a number of years, and where infection, gangrene and ulcers are present. In the application of the invention to diabetes subjects with special skin and circulation considerations or where a hypoallergenic magnet is required a platinum or 24 K gold coated circular magnet of 100 to 9,000 gauss can be attached, mounted or implanted in the pancreas gland point in the auricle of the left ear. Irrespective of the method of attachment or placement, the invention provides for the effective control of the level of blood sugar while insulin or an oral hypoglycemic agent is taken by the subject. The medications are generally taken by insulin injection for subjects having insulin-dependent diabetes mellitus or by the taking of oral hypoglycemic agents for those subjects having non-insulin-dependent diabetes mellitus.

Figure 3:
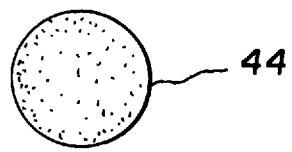
FIG. 3 is a top plan view of a prior art circular adhesive plaster.

Referring now to FIG. 1 the best mode of the invention is illustrated wherein left ear 10 includes an outer rim 12, an ear lobe 14 and an auditory canal 16. Surrounding the auditory canal and channelling sound to the auditory canal 16 is the auricle 18 having somewhat of a U-shaped configuration. The origin of outer rim 12 of ear 10 begins in auricle 18 and curves around to ear lobe 14. The origin of outer rim 12 in auricle 18 exits auricle 18 at exit point or beginning of the helix crus 20. From the beginning of the helix crus 20 to the end of the helix crus 22 in auricle 18 a line 24 can be drawn from the end of the helix crus 22 to the beginning of the helix crus 20. Line 24 can be divided into four equal segments and a line 26 can be drawn from the last quarter segment of the helix crus substantially perpendicular to the outer rim origin in the auricle to the central rim 28. Midway between the ends of line 26 is the pancreas gland point 30 which is the preferred and primary location for attaching a magnet to the ear with a prior art adhesive plaster 44 (FIG. 3). The pancreas gland point 30 is located only in the left ear and is the primary location for the attachment or implantation of a magnetic device in accordance with the invention. Pancreas gland point 30 is easily accessed from the front side for mechanical attachment of a prior art magnetic device or a hypoallergenic magnetic device constructed in accordance with the invention. In addition a special implantable magnetic device constructed in accordance with the invention may be implanted at pancreas gland point 30 from either the front side or on the reverse side of left ear 10.

Unlike the pancreas gland point 30 which is only located in the auricle of the left ear, the secondary locations of the thalamus point and central rim point are located in both the right and left ear. The location of the secondary locations of the thalamus point and central rim point in both the left and right ears allows magnets to be attached or alternatively rotated between the left and right ears in the treatment of diabetes in the human patient or subject.

Figure 2:
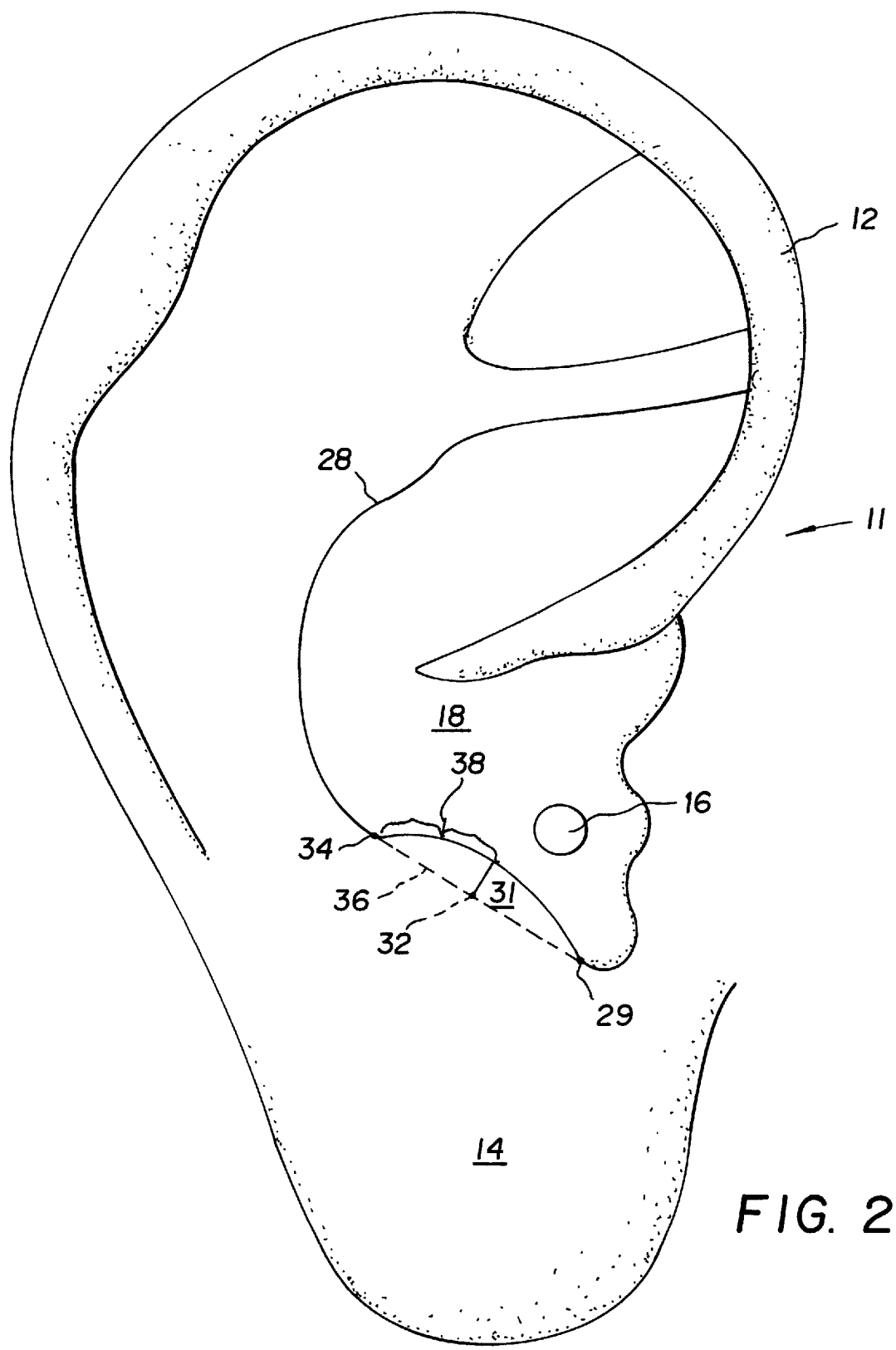
FIG. 2 is a side view of the right ear of a human subject.

Referring now to FIG. 1 and 2 the right ear 11 is illustrated in which similar portions have been numbered consistently with FIG. 1. In both the left ear 10 and right ear 11 below the auditory canal 16 and located midway between the beginning of the antitragus 29 in auricle 18 and the helix tragus notch 34 on the central rim 28 and behind the antitragus 31 on the middle line of the antitragus 36 is the thalamus point 32. Located midway between thalamus point 32 and the helix tragus notch 34 on central rim 28 and on central rim 28 is the central rim point 38. Thalamus point 32 and central rim point 38 are both secondary or supplemental positions for the placement of additional magnets to assist in the stabilization and control of the blood sugar levels in diabetic subjects as will be described hereinafter in greater detail.

Figure 4:
FIG. 4 is a perspective view of a prior art magnetic disk utilized in accordance with the invention.
Figure 5:
FIG. 5 is a top plan view of FIG. 4.
Figure 6:
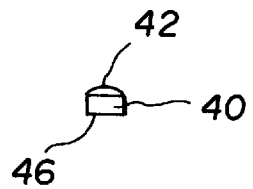
FIG. 6 is a side elevational view of FIG. 5.

Referring now to FIGS. 4, 5 and 6, a prior art magnetic disk 40 is illustrated which is circular in configuration having a diameter of about 0.5 cm and a thickness of about 0.13 cm which as illustrated in FIG. 6 is the side elevation view of the magnet and includes a slightly rounded top 42. The prior art magnetic disk may be obtained from OMS Medical Supply Co. of Braintree, Mass. and is typically made of an alloy of iron and barium although other types of magnetic alloy materials may be used such as niobium, titanium or other magnetic material. The strength of available prior art magnetic disk 40 is in the range of 100 to 9,000 gauss and preferably a kit in accordance with the invention includes a variety of magnets varying in magnet strength from 100 gauss to 9,000 gauss for attachment in the left and right ear of the human diabetic subject to assist in the regulation of blood sugar. The strength of the particular magnet selected for the regulation of the blood sugar depends upon age of the diabetic subject and the stage of the disease as well as the effectiveness of the particular strength of the magnet in controlling the level of blood sugar of the particular diabetic subject.

In the application of the invention to a diabetic adult subject or children above the age of 6 (six) may be treated with initially an 800 gauss magnetic disk at the pancreas gland point 30 in the left ear and their blood sugar monitored to determine the effectiveness of the magnet. Where an 800 gauss magnetic disk is sufficient, the strength of the magnetic disk need not be increased. However, where there is an advanced case of diabetes or poor circulation, a magnetic disk in the range of 2,500 may be required. Children under the age of six and particularly infants can be initially treated with a 100 gauss magnetic disk. Children under the age of 6 can use a 100 to 400 gauss magnet, whereas children above 6 and adults are treated with magnets from 800 gauss to 9,000 gauss. The strength of the magnet depends on the age, stage of the disease, the sensitivity of the patient to the magnet and effectiveness of the magnet in regulating blood sugar together with insulin or oral hypoglycemic agent.

The prior art magnetic disk 40 as illustrated in FIGS. 4, 5 and 6, is a standard magnetic disk which may be obtained from OMS Medical Supplies of Braintree, Mass. The prior art magnetic disk 40 does not include a hypoallergenic coating of platinum and is not made of a hypoallergenic alloy to prevent skin reactions in sensitive persons or persons with advanced stages of the disease who require special considerations. Hypoallergenic magnetic disks constructed in accordance with the invention will be described hereinafter in greater detail.

Referring now to FIG. 3 a prior art small adhesive circular plaster 44 is illustrated which is utilized to fix magnetic disk 40 to the left and right ear and preferably to pancreas gland point 30 which is only in the left ear of a patient. Adhesive plaster 44 is round, 1.5 cm in diameter or oval 1.4 cm×1.3 cm and is made of cloth material with a tacky, sticky back surface which is utilized to attach and position magnetic disk 40 on pancreas gland point 30 of the left ear of a patient.

The flat side 46 (FIG. 6) of magnetic disk 40 is maintained against the skin at the pancreas gland point 30 of the left ear for 24 hours a day for a period of one to two weeks at which point magnetic disk 40 and adhesive plaster 44 are removed, at which time the magnetic disk 40 and the skin of the ear are cleaned, preferably with rubbing alcohol, and replaced with a new adhesive plaster 44 on pancreas gland point 30 in the left ear of the human diabetic subject.

The blood sugar of the human diabetic patient is then preferably checked on a daily basis while insulin or hypoglycemic agents should be adjusted and administered as recommended by the physician. The effectiveness of the magnetic disk can be determined by daily monitoring of the blood sugar. Generally, if the proper strength of the magnetic disk has been selected, previous levels of blood sugar will not only drop but will be maintained at a lower and steadier level. Where the blood sugar is lowered or becomes too low as a result of the regulating effect of the magnetic disk in combination with insulin or hypoglycemic agent, the dose of the insulin or oral hypoglycemic agent can be reduced according to recommendation of the physician.

In applications where an 800 gauss magnetic disk appears to have little or no effect on the blood sugar the 800 gauss magnetic disk should be increased to a higher gauss level magnet of up to 9,000 gauss. The increase in the strength of the magnet should be accomplished with a constant monitoring of the blood sugar as well as the usual taking of insulin or hypoglycemic agent to determine at what point the strength of the magnetic disk results in desired regulation of the blood sugar and possibly a drop in the blood sugar utilizing the previously prescribed dosage of insulin or hypoglycemic agent.

In some cases more than one magnetic disk can be effectively utilized in the ear of the human subject. In such cases the second magnetic disk can be placed in thalamus point 32 alone or in addition to central rim point 38 to assist in the regulation of blood sugar levels of the subject. In all such cases the application of additional magnets plus the strength of the additional magnetic disks are selected based upon the age and sensitivity of the individual, the stage of the disease as well as the effectiveness of the strength of each additional magnetic disk. The application of multiple magnets is dependent upon the results of a daily check of blood sugar level together with the normal dosage of either insulin or a hypoglycemic agent.

The placement of the magnet in the ear of the human subject is important in that the center of the magnetic disk should not be more than two millimeters away from pancreas gland point 30 in the left ear or thalamus point 32 or central rim point 40 (in either the right ear or left ear). It is equally important the subject continue taking insulin or an oral hypoglycemic agent together with the application of the magnetic disk to determine at what point the blood sugar is best stabilized and preferably reduced to a lower level given a particular dosage of insulin or an oral hypoglycemic agent.

Various types of injectable natural insulin made from human, pork, beef and beef-pork mixtures may be utilized and are known to those skilled in the art as NPH, Lente, Mixtard, Regular Semilente, Ultralente and Protamine Zinc. In addition to these natural-based insulins synthetic human insulins may be made by recombinant DNA techniques. Various semi-synthetic insulins are made by replacing an amino acid of insulin of animal origins. Synthetic human insulins are made by recombinant DNA techniques. Tradenames of such synthetic or semi-synthetic insulins are Humulin and Novolin and possibly others. Insulin-dependent diabetics take the recommended injection of insulin in combination with utilizing the magnet in the ear. The recommended strength of the magnetic disk is the disk having a magnetic strength where a given dosage of insulin results in a lower level of blood sugar than is maintained by insulin alone. In this regard the blood sugar levels should be constantly monitored with the normal injection of insulin and the strength of the magnetic disk increased to possibly allow a reduction in the dosage of insulin to best determine the level of most effectiveness of the combination of both the insulin and magnetic disk.

The method of the invention can also be used in non-insulin-dependent diabetics. In the case of non-insulin-dependent diabetics various hypoglycemic agents are taken orally to assist in the regulation of blood sugar. These oral hypoglycemic agents referred to generically as Glyburide, Chlorpropamide, Acetohexamide, Glipizide, Tolbutamide and Tolazamide. These oral hypoglycemic agents in addition to Humalog which is under study by the FDA can be used in accordance with the invention. The invention allows the dosages of these drugs to be reduced which assists in reducing the problems of drug interaction and complications resulting from the long term use of oral hypoglycemic agents. These oral hypoglycemic agents are taken by the diabetic subject and the magnetic disks utilized to determine the effectiveness of the combination of the magnetic disk with the oral hypoglycemic agent. The combination of oral hypoglycemic agent and magnetic disk is monitored by a periodic and preferably daily check of blood sugar to determine the effectiveness of the combination and to determine a point where the oral hypoglycemic agent together with the magnetic disk best lowers and stabilizes the blood sugar level.

Figure 7:
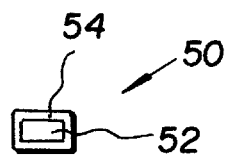
FIG. 7 is a side elevational view in section of a novel hypoallergenic magnetic disk similar to FIG. 4 but which includes a hypoallergenic coating of platinum.

The method of the invention in its preferred embodiment utilizes one or more cylindrical magnetic disks coated with a hypoallergenic agent or made of a hypoallergenic material which is attached externally or may be implanted. Such hypoallergenic magnets are particularly desirable in the case of aged or advanced stage diseased subjects where circulation problems or other factors result in an increased sensitivity of the skin or where risks of infection are present. Referring now to FIG. 7 a novel magnetic disk 50 for external application is illustrated in section, wherein the core of the magnetic disk 52 is composed of a magnetic substance from between 100 to 9,000 gauss and the exterior of the magnet is coated with a hypoallergenic substance that does not interfere with the magnetic properties of the magnetic core 52. Coating 54, for example, can be platinum, 24 K gold or other hypoallergenic material which does not reduce the magnetic properties of the magnetic disk and provides additional advantages in preventing infection or allergic reactions in diabetic subjects with sensitive skin or that may be susceptible to infection due to advanced stages of diabetes, aging or other problems presenting a risk of infection.

Figure 8:
FIG. 8 is a perspective view of a novel implantable hypoallergenic magnetic implant constructed in accordance with the invention.

The method of the invention in its preferred application includes an implantable hypoallergenic magnetic material composed of platinum, titanium or alloy of platinum or titanium. The preferred implantable magnet is illustrated in a magnified format in FIG. 8 and is a hypoallergenic magnet 60 for implanting at the pancreas gland point 30 at the front or primarily the back side of the left ear. Hypoallergenic magnet 60 may also be implanted in the left or right ear at thalamus point 32 and central rim point 40. Hypoallergenic magnet 60 is preferably composed of a platinum alloy having a strength of 100 to 9,000 gauss and is about 3 to 5 millimeters wide. Other magnetic materials may be utilized including titanium and niobium and various metal alloys of iron which have magnetic strengths of up to 14,000 gauss. Such implantable magnets can also be utilized for implantation when coated with a hypoallergenic coating. Since there are many variations in shape and thickness of the human ear, in some cases, a smaller magnet should be used for implantation.

The best mode of the present invention will be described hereinafter in greater detail with respect to the following Examples:

Example I

A 59-year old male subject weighing approximately 150 pounds having insulin-dependent diabetes type II for 20 years was treated in accordance with the invention. The diabetic subject had previously had his lower left leg amputated because of a previous infection. The diabetic subject had for four months been treated with antibiotics at Johns Hopkins Hospital since the right foot had become infected about four months prior to treatment in accordance with this invention. The antibiotics treatment at Johns Hopkins Hospital did not work and antibiotics had been discontinued and surgery had been planned to now amputate the right foot.

The right foot and leg was red, swollen and pus was coming out of the first and fourth toes and heel, and gangrene had formed on the fourth toe and heel. The right foot also emitted a terrible odor.

The initial treatment consisted of scalp acupuncture and treatment with Chinese herbs to control the infection. The herbal treatment utilized included the herbs Herba Taraxaci Mongolici cum Radice (botanical name: *Taraxacum mongolicum* Hand.-Mazz.) and Herba cum Radice Violae Yedoensitis (botanical name: *Viola yedoensis* Mak). Both herbs are reported in *Materia Medica*, Bensky & Gamble as having activity for reducing swelling and reducing abscesses but do not lower blood sugar.

Approximately one and a half weeks later the diabetic subject visited the office for a second treatment and the swelling on the right foot had subsided. Approximately one week thereafter the diabetic subject visited a third time and the swelling had been reduced but the right foot still emitted a terrible odor and the blood sugar was still high, being about 200 milligrams per deciliter (mg/dl.) even though the subject continued to use insulin. Due to the age of the diabetic subject as well as the possibility of infection due to bad circulation and possible complications with acupuncture a 2,500 gauss magnetic disk was attached to pancreas gland point 30 (FIG. 1) in the left ear while the subject continued to take insulin.

Two days after the diabetic subject began treatment with the prior art magnetic disk, as illustrated in FIGS. 3, 4 and 5 and discussed herein, the blood sugar decreased. Approximately 1 week later the swelling of the right foot had been remarkably reduced and the smell from the foot was not as bad. The Doctor at Johns Hopkins Hospital found new tissue growing in the right foot and the diabetic subject was advised by the Doctor at Johns Hopkins Hospital that he was surprised to see the growth of new tissue and decided against surgery on the right foot.

Thereafter the diabetic subject continued to visit about once a week and continued to take insulin and wear the 2,500 magnetic disk in the left ear at pancreas gland point 30 (FIG. 1) which resulted in the stabilization of the blood sugar at 125 mg/dl. and at times even lower. Approximately 8 months later blood flow was measured in the subject's right foot by Johns Hopkins Hospital and blood flow was found to have increased, the pus had disappeared and seven layers of new tissue were growing. The subject continues to wear a circular magnetic disk of 2,500 gauss in combination with normal insulin treatment, and the blood sugar has been controlled and regulated at about 100 mg/dl. with the growth of new tissue and the disappearance of the gangrene in the fourth toe and reduced in the heel.

The circular 2,500 gauss magnetic disk worn at the pancreas gland point in the left ear along with insulin injection controlled the blood sugar of the diabetic subject at a lower level that could not be controlled by insulin alone and with the control of the blood sugar the body was able to eliminate the infection and gangrene. Daily data on blood sugar measurements before and after treatment with the magnetic disk are reproduced below in Table IA and Table IB respectively.

TABLE IA

Daily Record Before Therapy:

| DATE 1995 | TIME OF DAY | BLOOD SUGAR mg/dl. | INSULIN TYPE & DOSE | OTHER MEDICATION FOR DIABETES | NOTES |
|---|---|---|---|---|---|
| Before 5/4/1995 | Morning | 250 | 28 R | | Before Magnet Treatment Average Was 200–250 mg/dl. |
| | Evening | 300 | 15 NPH | | |
| | Morning | 210 | 28 R | | |
| | Evening | 225 | 15 NPH | | |
| | Morning | | | | |
| | Evening | | | | |

TABLE IB

Daily Record After Therapy:

| DATE 1996 | TIME OF DAY | BLOOD SUGAR mg/dl. | INSULIN TYPE & DOSE | OTHER MEDICATION FOR DIABETES | NOTES |
|---|---|---|---|---|---|
| Before | Morning | 120 | 15 R | | |
| 3/7/1996 | Evening | 135 | 10/NPH | | |
| 3/8/1996 | Morning | 127 | 15 R | | |
| | Evening | 140 | 10/NPH | | |
| 3/9/1996 | Morning | 123 | 15 R | | |
| | Evening | 175 | 10 NPH | | |
| 3/10/1996 | Morning | 110 | 15 R | | |
| | Evening | 147 | 10 NPH | | |
| 3/11/1996 | Morning | 117 | 15 R | | |
| | Evening | 145 | 10 NPH | | |
| 3/12/1996 | Morning | 120 | 15 R | | |
| | Evening | 174 | 10 NPH | | |
| 3/13/1996 | Morning | 114 | 15 R | | |
| | Evening | 175 | 10 NPH | | |
| 3/14/1996 | Morning | 137 | 15 R | | |
| | Evening | 125 | 10 NPH | | |
| 3/15/1996 | Morning | 77 | 15 R | | |
| | Evening | 192 | 10 NPH | | |
| 3/16/1996 | Morning | 107 | 15 R | | |
| | Evening | 124 | 10 NPH | | |
| 3/17/1996 | Morning | 69 | 15 R | | |
| | Evening | 145 | 10 NPH | | |
| 3/18/1996 | Morning | 91 | 15 R | | |
| | Evening | 163 | 10 NPH | | |
| 3/19/1996 | Morning | 110 | 15 R | | |
| | Evening | 183 | 10 NPH | | |
| 3/20/1996 | Morning | 70 | 15 R | | |
| | Evening | 190 | 10 NPH | | |
| 3/21/1996 | Morning | 80 | 15 R | | |
| | Evening | 181 | 10 NPH | | |
| 3/22/1996 | Morning | 157 | 15 R | | |
| | Evening | 84 | 10 NPH | | |
| 3/23/1996 | Morning | 111 | 15 R | | |
| | Evening | 147 | 10 NPH | | |
| 3/24/1996 | Morning | 92 | 15 R | | |
| | Evening | 162 | 10 NPH | | |
| 3/25/1996 | Morning | 77 | 15 R | | |
| | Evening | 132 | 10 NPH | | |
| 3/26/1996 | Morning | 122 | 15 R | | |
| | Evening | 84 | 10 NPH | | |
| 3/27/1996 | Morning | 121 | 15 R | | |
| | Evening | 105 | 10 NPH | | |

| | (Blood sugar mg/dl.) | |
|---|---|---|
| | Before Magnet Treatment | After Magnet Treatment |
| $\bar{X}$ | B 246.25 | A 127.74 |
| n | 4 | 42 |
| SD | 34.16 | 34.20 |
| SE | 17.08 | 5.28 |

$\bar{X}_B - \bar{X}_A = 118.51$ degree of freedom=44

$$t = \frac{118.51}{\sqrt{297.72 + 27.88}} = \frac{118.52}{17.88} = 6.63$$

P<0.001

Where $\bar{X}$ means average, where R means regular insulin, where NPH means neutral protein Hagedorn (long lasting) insulin, where n means number of times the blood sugar was measured, where SD means standard deviation, where SE means standard error.

Note: Due to the subject's change of residence all the blood sugar data before treatment could not be located. Only 4 figures could be obtained which were used. The before treatment average was 200–250 with insulin 28/15 before treatment. After treatment the average blood sugar is 127.74 with insulin 15/10.

Example II

In this Example a 55-year old man, weighing approximately 168 pounds, suffering from type II diabetes for about 15 years was treated in accordance with the invention. About 1.5 years after the diagnosis of diabetes the subject had to change from an oral hypoglycemic medication to insulin injection in order to control his blood sugar. The blood sugar was in the range of 140 to 200 mg/dl. The diabetic subject had no hair on the top of the head. Treatment was initiated by utilizing an 800 gauss magnetic disk at the pancreas gland point 30 (FIG. 1) in the left ear. Two days later after the attachment of a circular magnetic disk to the left ear the blood sugar had decreased and became stable at about 100 to 120 mg/dl. while the subject continued to take insulin.

About two weeks after starting treatment with the circular magnetic disk and insulin the subject reported that hair began to grow on the top of his head. When the subject was again seen about two months later some of the new hair was about 1.5 inches long.

The diabetic subject worked long hours, missed lunch and sometimes ate sweets. When the diabetic subject ate sweets the blood sugar became high, otherwise the 800 gauss magnetic disk together with insulin injections controlled the blood sugar within the 100 to 120 mg/dl. range. Daily data on blood sugar measurements before and after treatment with the magnetic disk are reproduced below in Table IIA and Table IIB respectively.

TABLE IIA

Daily Record Before Therapy:

| DATE 1995 December | TIME OF DAY | BLOOD SUGAR mg/dl. | INSULIN TYPE & DOSE morning/evening | OTHER MEDICATION FOR DIABETES | NOTES |
|---|---|---|---|---|---|
| 12/2/1995 | Morning | 95 | 10 Regular/20 NPH | — | |
|  | Evening | 148 | 10 Regular/20 NPH | | |
| 12/3/1995 | Morning | 141 | 10 Regular/20 NPH | | |
|  | Evening | 134 | 10 Regular/20 NPH | | |
| 12/4/1995 | Morning | 120 | 10 Regular/20 NPH | | |
|  | Evening | 129 | 10 Regular/20 NPH | | |
| 12/5/1995 | Morning | 95 | 10 Regular/20 NPH | | |
|  | Evening | 150 | 10 Regular/20 NPH | | |
| 12/6/1995 | Morning | 165 | 10 Regular/20 NPH | | |
|  | Evening | 247 | 12 R/22 NPH | | |
| 12/9/1995 | Morning | 150 | 12 R/22 NPH | | |
|  | Evening | 367 | 15 R/25 NPH | | |
| 12/10/1995 | Morning | 87 | | | |
|  | Evening | 278 | 12 R/22 NPH | | |
| 12/11/1995 | Morning | 94 | 12 R/22 NPH | | |
|  | Evening | 190 | 12 R/22 NPH | | |
| 12/12/1995 | Morning | 175 | 12 R/22 NPH | | |
|  | Evening | 187 | 12 R/22 NPH | | |
| 12/13/1995 | Morning | 183 | 12 R/22 NPH | | |
|  | Evening | 273 | 12 R/22 NPH | | |
| 12/17/1995 | Morning | 99 | 12 R/22 NPH | | |
|  | Evening | 367 | 15 R/25 NPH | | |
| 12/18/1995 | Morning |  | 15 R/25 NPH | | |
|  | Evening | 278 | 12 R/25 NPH | | |
| 12/19/1995 | Morning | 163 | 12 R/25 NPH | | |
|  | Evening | 275 | 12 R/25 NPH | | |
| 12/20/1995 | Morning | 150 | 12 R/25 NPH | | |
|  | Evening | 185 | 12 R/25 NPH | | |
| 12/21/1995 | Morning | 165 | 12 R/25 NPH | | |
|  | Evening | 346 | 12 R/25 NPH | | |
| 12/22/1995 | Morning | 176 | 12 R/25 NPH | | |
|  | Evening | 238 | 12 R/25 NPH | | |
| 12/23/1995 | Morning | 188 | 12 R/25 NPH | | |
|  | Evening | 173 | 12 R/25 NPH | | |
| 12/24/1995 | Morning | 145 | 12 R/25 NPH | | |
|  | Evening | 284 | 12 R/25 NPH | | |
| 12/27/1995 | Morning | 165 | 12 R/25 NPH | | |
|  | Evening | 77 | 12 R/25 NPH | | |
| 12/28/1995 | Morning | 82 | 12 R/25 NPH | | |
|  | Evening | 150 | 12 R/25 NPH | | |
| 12/29/1995 | Morning | 140 | 12 R/25 NPH | | |
|  | Evening | 190 | 12 R/25 NPH | | |
| 12/30/1995 | Morning | 150 | 12 R/25 NPH | | |
|  | Evening | 200 | 12 R/25 NPH | | |

TABLE IIB

Daily Record After Therapy:

| DATE 1996 March–April | TIME OF DAY | BLOOD SUGAR mg/dl. | INSULIN TYPE & DOSE | OTHER MEDICATION FOR DIABETES | NOTES |
|---|---|---|---|---|---|
| 3/28/1996 | Morning | 179 | 10 R/ | — | |
|  | Evening | 134 | 20 NPH | | |
| 3/29/1996 | Morning | 127 | 10 R | | |
|  | Evening | 148 | 20 NPH | | |
| 3/30/1996 | Morning | 108 | 10 R | | |
|  | Evening | 203 | 20 NPH | | |
| 3/31/1996 | Morning | 135 | 10 R | | |
|  | Evening | 183 | 20 NPH | | |

TABLE IIB-continued

Daily Record After Therapy:

| DATE 1996 March–April | TIME OF DAY | BLOOD SUGAR mg/dl. | INSULIN TYPE & DOSE | OTHER MEDICATION FOR DIABETES | NOTES |
|---|---|---|---|---|---|
| 4/1/1996 | Morning | 74 | 10 R | | |
| | Evening | 81 | 20 NPH | | |
| 4/2/1996 | Morning | 86 | 10 R | | |
| | Evening | 175 | 20 NPH | | |
| 4/3/1996 | Morning | 99 | 10 R | | |
| | Evening | 92 | 20 NPH | | |
| 4/4/1996 | Morning | 90 | 10 R | | |
| | Evening | 140 | 20 NPH | | |
| 4/5/1996 | Morning | 76 | 10 R | | |
| | Evening | 151 | 20 NPH | | |
| 4/6/1996 | Morning | 101 | 10 R | | |
| | Evening | 112 | 20 NPH | | |
| 4/7/1996 | Morning | 106 | 10 R | | |
| | Evening | 164 | 20 NPH | | |
| 4/8/1996 | Morning | 145 | 10 R | | |
| | Evening | | 20 NPH | | |
| 4/9/1996 | Morning | 83 | 10 R | | |
| | Evening | 158 | 20 NPH | | |
| 4/10/1996 | Morning | 147 | 10 R | | |
| | Evening | | 20 NPH | | |
| 4/11/1996 | Morning | | 10 R | | |
| | Evening | 149 | 20 NPH | | |
| 4/12/1996 | Morning | 124 | 10 R | | |
| | Evening | 250 | 20 NPH | | |
| 4/13/1996 | Morning | 141 | 10 R | | |
| | Evening | 169 | 20 NPH | | |
| 4/14/1996 | Morning | 105 | 10 R | | |
| | Evening | 136 | 20 NPH | | |
| 4/15/1996 | Morning | 112 | 10 R | | |
| | Evening | 105 | 20 NPH | | |
| 4/16/1996 | Morning | 130 | 10 R | | |
| | Evening | 242 | 20 NPH | | |
| 4/17/1996 | Morning | 98 | 10 R | | |
| | Evening | 137 | 20 NPH | | |

| | (Blood sugar mg/dl.) | |
|---|---|---|
| | Before Magnet Treatment | After Magnet Treatment |
| $\bar{X}$ | 180.98 | 132.71 |
| n | 43. | 39 |
| SD | 74.28 | 41.18 |
| SE | 11.33 | 6.59 |

$\bar{X}_B - \bar{X}_A = 180.98 - 132.71 = 48.27$ degree of freedom=80

$$t = \frac{48.27}{\sqrt{129.50 + 43.43}} = \frac{48.22}{13.15} = 3.67$$

P<0.001

Where $\bar{X}$ means average, where R means regular insulin, where NPH means neutral protein Hagedorn (long lasting) insulin, where n means number of times the blood sugar was measured, where SD means standard deviation, where SE means standard error.

Example III

In this Example a 56-year old white female, weighing approximately 250 pounds had suffered from IDDM for 20 years and lower back pain for 1 year. The pain radiated to the left leg. The patient had been using 70/30 Humulin, 40/45 units daily.

Initially the patient was treated with a 24 K gold-plated 2,500 gauss magnet affixed with a plaster in the left ear at the pancreas gland point 30 (FIG. 1) for 16 days. The blood sugar decreased some but not satisfactorily. Thereafter a 6,000 gauss magnet was used on the same point, namely the pancreas gland point, and the blood sugar decreased more.

Statistics show the 6,000 gauss treatment lowered the blood sugar significantly as compared with before treatment. The patient's skin was sensitive to this 24 K gold plate, so an adhesive paper was used to cover the gold surface of the magnet. Although the lower back pain was treated by acupuncture the pain appears to have been further reduced when the blood sugar went down. Daily data on blood sugar measurements before and after treatment with the magnetic disc of 2,500 gauss and 6,000 gauss are reproduced below in Table IIIA and Table IIIB respectively.

TABLE IIIA

Daily Record Before Therapy:

| DATE 1996 M/D/Y | TIME OF DAY | BLOOD SUGAR mg/dl. | INSULIN TYPE & DOSE 70/30 Humulin Insulin/ 70/30 Humulin Insulin morning/evening | OTHER MEDICATION FOR DIABETES | NOTES |
|---|---|---|---|---|---|
| 6/1/1996 | Morning | 186 | 42–45/20–25 | | |
| | Evening | 286 | (unit) (unit) | | |
| 6/2/1996 | Morning | 172 | 42–45/20–25 | | |
| | Evening | 192 | (unit) (unit) | | |
| 6/3/1996 | Morning | 119 | 42–45/20–25 | | |
| | Evening | | (unit) (unit) | | |
| 6/4/1996 | Morning | 226 | 42–45/20–25 | | |
| | Evening | | (unit) (unit) | | |
| 6/5/1996 | Morning | 182 | 42–45/20–25 | | |
| | Evening | 151 | (unit) (unit) | | |
| 6/6/1996 | Morning | 221 | 42–45/20–25 | | |
| | Evening | 148 | (unit) (unit) | | |
| 6/7/1996 | Morning | 198 | 42–45/20–25 | | |
| | Evening | | (unit) (unit) | | |
| 6/8/1996 | Morning | 198 | 42–45/20–25 | | |
| | Evening | | (unit) (unit) | | |
| 6/9/1996 | Morning | 188 | 42–45/20–25 | | |
| | Evening | | (unit) (unit) | | |
| 6/10/1996 | Morning | 178 | 42–45/20–25 | | |
| | Evening | 198 | (unit) (unit) | | |
| 6/11/1996 | Morning | 183 | 42–45/20–25 | | |
| | Evening | 97 | (unit) (unit) | | |
| 6/12/1996 | Morning | 133 | 42–45/20–25 | | |
| | Evening | 184 | (unit) (unit) | | |
| 6/13/1996 | Morning | 161 | 42–45/20–25 | | |
| | Evening | | (unit) (unit) | | |
| 6/14/1996 | Morning | 175 | 42–45/20–25 | | |
| | Evening | 199 | (unit) (unit) | | |
| 6/15/1996 | Morning | 165 | 42–45/20–25 | | |
| | Evening | 198 | (unit) (unit) | | |
| 6/16/1996 | Morning | 168 | 42–45/20–25 | | |
| | Evening | | (unit) (unit) | | |
| 6/17/1996 | Morning | 289 | 42–45/20–25 | | |
| | Evening | 119 | (unit) (unit) | | |
| 6/18/1996 | Morning | 189 | 42–45/20–25 | | |

TABLE IIIB

Daily Record After Therapy:

| DATE 1996 M/D/Y | TIME OF DAY | BLOOD SUGAR mg/dl. | INSULIN TYPE & DOSE 70/30 Humulin Insulin/ 70/30 Humulin Insulin morning/evening | OTHER MEDICATION FOR DIABETES | NOTES |
|---|---|---|---|---|---|
| 6/18/1996 | Evening | 123 | | 2500 Gs mag- | net |
| 6/19/1996 | Morning | 145 | 42/45/20–22 | starting at | 3 pm |
| | Evening | 156 | " | in left ear | pan- |
| 6/20/1996 | Morning | 187 | " | creas gland | point |
| | Evening | 194 | " | | |
| 6/21/1996 | Morning | 154 | " | | |
| | Evening | 168 | " | | |
| 6/22/1996 | Morning | 178 | 42/45/20–22 unit | | |
| | Evening | | " | | |
| 6/23/1996 | Morning | 183 | 42–45/20–25 unit | | |
| | Evening | 188 | " | | |
| 6/24/1996 | Morning | 191 | " | | |
| | Evening | 172 | " | | |
| 6/25/1996 | Morning | 139 | " | | |
| | Evening | | " | | |
| 6/26/1996 | Morning | 173 | " | | |
| | Evening | 128 | " | | |
| 6/27/1996 | Morning | 188 | " | using magnet | |
| | Evening | 242 | " | only for 3 | |
| 6/28/1996 | Morning | 184 | " | days because | |
| | Evening | 143 | " | she has | |
| 6/29/1996 | Morning | 192 | " | reaction to | |
| | Evening | 114 | " | gold in ear. | |
| 6/30/1996 | Morning | 168 | " | | |

TABLE IIIB-continued

Daily Record After Therapy:

| DATE 1996 M/D/Y | TIME OF DAY | BLOOD SUGAR mg/dl. | INSULIN TYPE & DOSE 70/30 Humulin Insulin/ 70/30 Humulin Insulin morning/evening | OTHER MEDICATION FOR DIABETES | NOTES |
|---|---|---|---|---|---|
| | Evening | | " | | |
| 7/1/1996 | Morning | 154 | " | | |
| | Evening | 126 | " | | |
| 7/2/1996 | Morning | 163 | " | | |
| | Evening | | " | | |
| 7/3/1996 | Morning | | " | | |
| | | at 6 pm pancreas covered by a In this way reaction | change to 6,000 gs gland point. The thin layer of she does not have with gold. | magnet in magnet is paper tape. skin | |
| | Evening | | change to 6,000 gs gland point. The thin layer of she does not have with gold. | | |
| 7/4/1996 | Morning | 168 | change to 6,000 gs gland point. The thin layer of she does not have with gold. | | |
| | Evening | | change to 6,000 gs gland point. The thin layer of she does not have with gold. | | |
| 7/5/1996 | Morning | 192 | change to 6,000 gs gland point. The thin layer of she does not have with gold. | | |
| | Evening | | change to 6,000 gs gland point. The thin layer of she does not have with gold. | | |
| 7/6/1996 | Morning | 156 | change to 6,000 gs gland point. The thin layer of she does not have with gold. | | |
| | Evening | | change to 6,000 gs gland point. The thin layer of she does not have with gold. | | |
| 7/7/1996 | Morning | 139 | change to 6,000 gs gland point. The thin layer of she does not have with gold. | | |
| | Evening | 119 | change to 6,000 gs gland point. The thin layer of she does not have with gold. | | |
| 7/8/1996 | Morning | 143 | 42–45/20–25 unit | | |
| | Evening | 157 | " | | |
| 7/9/1996 | Morning | 174 | " | | |
| | Evening | 138 | " | | |
| 7/10/1996 | Morning | 75 | " | | |
| | Evening | 167 | " | | |
| 7/11/1996 | Morning | 181 | " | | |
| | Evening | 242 | " | | drank reg. coke |
| 7/12/1996 | Morning | 158 | " | | |
| | Evening | 144 | " | | |
| 7/13/1996 | Morning | 161 | " | | |
| | Evening | 95 | " | | |
| 7/14/1996 | Morning | 171 | " | | |
| | Evening | 117 | " | | |

TABLE IIIB-continued

Daily Record After Therapy:

| DATE 1996 M/D/Y | TIME OF DAY | BLOOD SUGAR mg/dl. | INSULIN TYPE & DOSE 70/30 Humulin Insulin/ 70/30 Humulin Insulin morning/evening | OTHER MEDICATION FOR DIABETES | NOTES |
|---|---|---|---|---|---|
| 7/15/1996 | Morning | 165 | " | | |
| | Evening | 165 | " | | |
| 7/16/1996 | Morning | 141 | " | | |
| | Evening | 121 | " | | |
| 7/17/1996 | Morning | 155 | " | | |
| | Evening | 122 | " | | |
| 7/18/1996 | Morning | 131 | " | | |
| | Evening | 116 | " | | |
| 7/19/1996 | Morning | 137 | " | | |
| | Evening | 252 | " | | sweet food |
| 7/20/1996 | Morning | 132 | " | | |
| | Evening | 144 | " | | |
| 7/21/1996 | Morning | 119 | " | | |
| | Evening | 113 | " | | |
| 7/22/1996 | Morning | 152 | " | | |
| | Evening | 192 | " | | sweet jelly |
| 7/23/1996 | Morning | 119 | " | | |
| | Evening | | " | | |
| | | | after using 6,000 does not crave night any more | gauss, she candy at | |

2,500 gauss $\overline{X}_B - \overline{X}_A = 182.25 - 166.12 = 16.13$ before after $N_B = 28 \ N_A = 25 \ \text{total} \ N = 53$ $SD_B = 41.41 \ SD_A = 28.15$ $SE_B = 7.83 = \dfrac{41.41}{\sqrt{28}} = 7.83 \ SE_B = 5.63 = \dfrac{28.15}{\sqrt{25}} = 5.63$ $t = \dfrac{16.13}{\sqrt{(7.83)^2 + (5.63)^2}} =$ $\dfrac{16.13}{\sqrt{61.3 + 31.7}} = \dfrac{16.13}{\sqrt{93}} = \dfrac{16.13}{9.64} = 1.67$ degree of freedom = 28+25 = 53−1 = 52

P>0.05 not sig. (this is from chart) 6,000 gauss

| Before Magnet Treatment | After Magnet Treatment |
|---|---|
| (Blood sugar mg/dl.) | |
| $\overline{X}B = 182.25$ | $\overline{X}A = 149.28$ |
| n = 28 | n = 36 including previous data |
| SD = 41.41 | SD = 34.89 |
| $SE = \dfrac{41.41}{\sqrt{28}} = 7.83$ | $SE = \dfrac{34.87}{\sqrt{36}} = 5.82$ |

$\overline{X}_B - \overline{X}_A = 182.25 - 149.28 = 32.97$ $t = \dfrac{32.97}{\sqrt{(7.83)^2 + (5.82)^2}} = 3.38$ $P \leq 0.002$ Where $\overline{X}$ means average, where R means regular insulin, where NPH means neutral protein Hagedorn (long lasting) insulin, where n means number of times the blood sugar was measured, where SD means standard deviation, where SE means standard error.

In accordance with the invention magnets having a strength from about 100 to 14,000 gauss are attached or implanted in the ear of a human or animal subject and insulin injections or an oral hypoglycemic agent is administered to stabilize the blood sugar and assist in the regulation and control of the level of blood sugar between doses. For external use the circular magnetic disks may be utilized which may be composed of a variety of magnetic materials including barium iron alloy magnets having a magnetic strength of 100 to 9,000 gauss may be utilized as well as novel hypoallergenic magnets constructed of a hypoallergenic material and preferably platinum, titanium or hypoallergenic alloys to avoid infection and skin reaction due to poor circulation. The best magnets for use in accordance with the best mode of the invention include platinum-coated magnetic alloy disks of barium iron alloy, titanium and niobium as well as platinum and platinum-cobalt magnetic disks. Such hypoallergenic magnetic disks as well as those made from platinum alloy and platinum alloy with cobalt are preferred since they reduce the possibility of skin reaction and infection in subjects with hyperallergic skin or advanced stages of diabetes. In the preferred application of the invention magnets of platinum and platinum alloys are preferred for implantation. Such magnets have a magnetic strength in the range of 100 to 14,000 gauss.

In addition as discussed a kit can be provided for subjects with diabetes to assist them in achieving the advantages of the invention. The kit would preferably include one or more 100 gauss magnets, one or more 400 gauss magnets, one or more 800 gauss magnets, one or more 1,500 gauss magnets, one or more 2,000 gauss magnets, one or more 2,500 gauss magnets and one or more 3,000 gauss magnets, one or more 6,000 gauss magnets, one or more 9,000 gauss magnets for external application. The kit would also preferably include hypoallergenic magnets or include a hypoallergenic coating for external use to reduce the possibility of infection. The kit might also include a number of cloth adhesive plasters, diagram of both the left and right ear illustrating the pancreas gland point, thalamus point and central rim point together with a plastic model of the left ear to show the points of attachment of the magnetic discs. The kit might also optionally include instructions which advise the subject on increasing the strength of the magnet and placement of one or more magnetic disks in the ear. The instructions can also include the use of the magnet for children under 6 and infants, as well as instructions for comparing blood sugar levels with reference point standards. The instructions should also include warnings and limitations in applicability such as pace maker or other electrical device implanted in the body. The kit may optionally include a device for the daily measurement of blood sugar levels.

As will be recognized by those skilled in the art, the invention may be utilized and modified in a number of ways to achieve the regulation of blood sugar and a controlling of blood sugar within lower acceptable ranges or the reduction of insulin or hypoglycemic agents in the insulin-dependent and non-insulin-dependent subjects including humans and animals which have been generally referred to herein as subjects. The magnets may be of a configuration other than circular and may be attached in a number of different ways including surgical implantation in the ear of the subject. For example, the magnets may be made in a configuration other than circular and the thicknesses of the magnet varied depending upon their construction and composition as well as the materials from which the magnetic disk is constructed. The number and strength of the magnet can be increased and decreased dependent upon the particular requirements of the subject. These modifications as to the strength of the magnets as well as the modification of the magnets to include different types of hypoallergenic substances, alloys and coatings may be made to implement the invention in a variety of applications. It will be appreciated that these and other modifications can be made within the scope of the invention as defined in the following claims:

What is claimed is:

1. A method for the treatment of diabetes comprising:
   (a) placing a magnet in the ear at the pancreas gland point in the auricle of said ear; and
   (b) supplementing the pancreatic hormones of the subject.

2. The method for the treatment of diabetes of claim 1 wherein said step of placing said magnet is accomplished by placing said magnet in the left ear.

3. The method for the treatment of diabetes of claim 2 wherein said magnet is circular and has a magnetic strength of from about 100 to 14,000 gauss.

4. The method for the treatment of diabetes of claim 1 wherein said step of placing said magnet is accomplished by implanting said magnet in said ear and said magnet is a hypoallergenic magnet.

5. The method for the treatment of diabetes of claim 4 wherein said hypoallergenic magnet is a platinum alloy.

6. The method for the treatment of diabetes of claim 2 wherein a second magnet is placed in the thalamus point in the auricle of an ear of the subject.

7. The method for the treatment of diabetes of claim 2 wherein a second magnet is placed in the central rim point in the auricle of an ear of the subject.

8. The method for the treatment of diabetes of claim 2 wherein said step of supplementing said pancreatic hormones of said subject is provided by the administration of insulin.

9. The method for the treatment of diabetes of claim 2 wherein said step of supplementing said pancreatic hormones of said subject is provided by the administration of an oral hypoglycemic agent.

10. The method for the treatment of diabetes of claim 1 further comprising the step of placing a second magnet in the other ear of said subject.

11. The method for the treatment of diabetes of claim 10 wherein said second magnet is a circular magnet placed in the thalamus point of said other ear.

12. The method for the treatment of diabetes of claim 10 wherein said second magnet is a circular magnet placed in the central rim point of said other ear.

13. The method for the treatment of diabetes of claim 10 further comprising the step of maintaining a third magnet in the auricle of either ear of said subject.

14. A kit for the stabilization of blood sugar for the treatment of diabetes comprising:
   (a) a plurality of small magnets having a strength of from about 100 to 9,000 gauss;
   (b) an illustration of various locations in the auricle of the ear; and
   (c) means for mounting one of said plurality of small magnets in an ear of a patient.

15. The kit for the stabilization of blood sugar of claim 14 wherein said illustration is a plastic model of the left ear illustrating the pancreas gland point.

16. The kit for the stabilization of blood sugar of claim 14 wherein said plurality of small magnets are circular hypoallergenic magnetic disks each having a different strength in the range of about 100 to 9,000 gauss.

17. The kit for the stabilization of blood sugar of claim 15 wherein said plastic model also illustrates the thalamus point and central rim point.

18. The kit for the stabilization of blood sugar of claim 15 wherein said means for mounting one of said plurality of small magnets in an ear of a patient is an adhesive plaster.

19. The kit for the stabilization of blood sugar of claim 14 further comprising a blood sugar monitoring device.

20. A magnet for the treatment of diabetes comprising:
   (a) an implantable magnetic body having a strength of from about 100 to 14,000 gauss; and
   (b) constructed of a hypoallergenic material.

21. The magnet of claim 20 wherein said magnet is a platinum alloy having a magnetic strength of from about 100 to 9,000 gauss.

* * * * *